United States Patent [19]

Young et al.

[11] 4,414,972
[45] Nov. 15, 1983

[54] INHALATION DEVICE

[75] Inventors: David M. Young, Loughborough; Donald F. Mitchell, Diseworth, near Derby; Edward Amey, Loughborough, all of England

[73] Assignee: Fisons Limited, London, England

[21] Appl. No.: 287,887

[22] Filed: Jul. 29, 1981

[30] Foreign Application Priority Data

Aug. 4, 1980 [GB] United Kingdom ............... 8025385

[51] Int. Cl.³ .......................................... A61M 15/00
[52] U.S. Cl. ........................... 128/200.23; 128/203.15
[58] Field of Search ....................... 128/200.23, 203.15

[56] References Cited

U.S. PATENT DOCUMENTS 3,456,644  7/1969  Thiel .............................. 128/200.23

Primary Examiner—Henry J. Recla

Attorney, Agent, or Firm—Merriam, Marshall & Bicknell

[57] ABSTRACT

The present invention provides an inhalation device for use with a pressurized container having an outlet valve mechanism and from which material may be discharged by depression of a portion of the valve mechanism thereof, which device comprises a chamber for receiving said container; actuating means adapted to bear on the valve mechanism of the container; and first and second biasing means both adapted to bias the container towards the actuating means, said first and second biasing means each being of insufficient force alone to depress the portion of the valve mechanism of the container but together being of sufficient force to do so, said second biasing means being restrained in a position in which it does not bear on the container and releasable on inhalation through the device to a position in which it does bear on the container.

10 Claims, 1 Drawing Figure

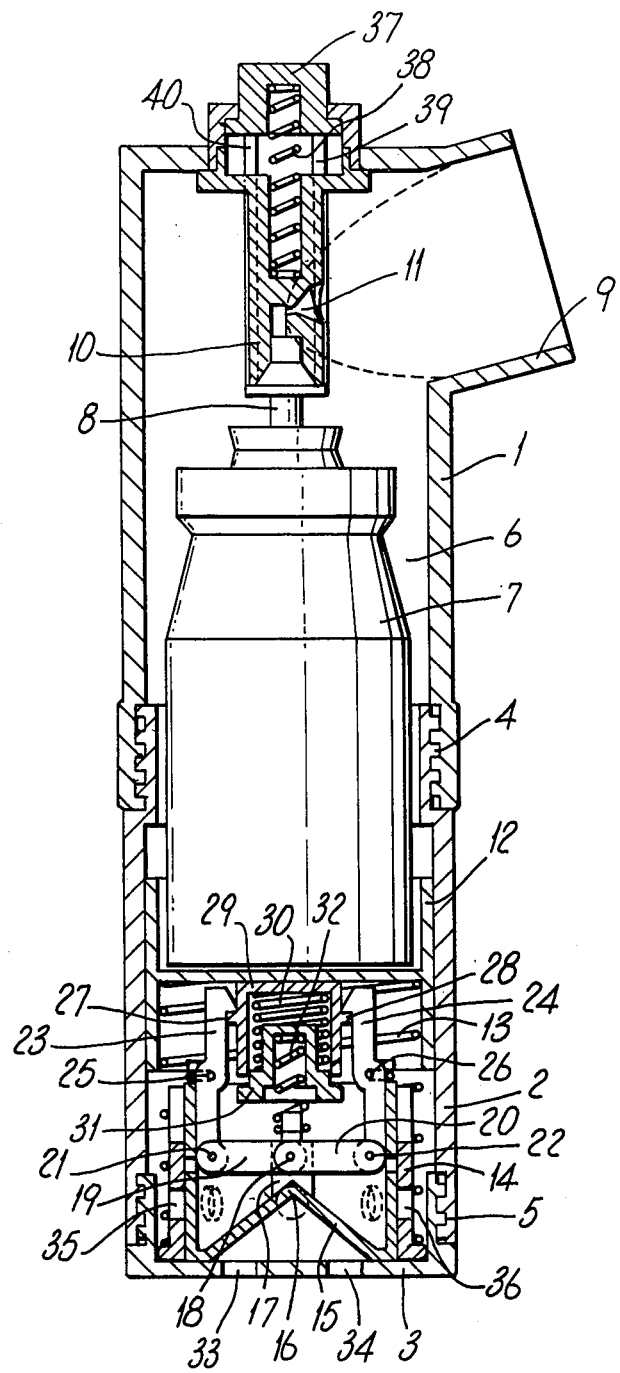

INHALATION DEVICE

This invention relates to an inhalation device for administering medicaments from pressurised containers.

Medicaments which are to be administered by inhalation, e.g. in the treatment of such diseases as asthma and hayfever, have for some time been provided in pressurised containers from which they are dispensed by actuation of a suitable valve mechanism in the outlet to the device. Usually such devices have incorporated a metering device so as to dispense a metered dose of medicament.

Inhalation devices of this kind have, however, required that the patient synchronise actuation of the valve with his breathing in through the device and this is often difficult for a user to achieve.

It has been proposed to cause expulsion of the metered dose of aerosol by, and thus automatically synchronise it with, inhalation through the device by the patient. Such devices have operated by means of a spring, which is initially restrained by a detent but which is released by the movement of a vane or diaphragm on inhalation by the patient. The spring then acts on the medicament container in such a way as to depress the outlet valve stem relative to the container and thus release the medicament. However, the force required to depress the valve stem of a conventional pressurised dispensing container (or aerosol can as it will hereinafter be denoted) is considerable and the actuating spring must be of even greater strength. Thus, operation of the valve is both sudden and violent, causing in some instances damage or discomfort to the mouth or nose of the patient. Also momentary cessation of inhalation due to surprise can be caused at the very moment when the medicament is released and must be inhaled.

The present invention provides an inhalation device which reduces these disadvantages and which is of compact construction and simple operation.

Accordingly, the present invention provides an inhalation device for use with a pressurised container having an outlet valve mechanism and from which material may be discharged by depression of a portion of the valve mechanism thereof, which device comprises a chamber for receiving said container; actuating means adapted to bear on the valve mechanism of the container; and first and second biasing means both adapted to bias the container towards the actuating means, said first and second biassing means each being of insufficient force alone to depress the portion of the valve mechanism of the container but together being of sufficient force to do so, said second biassing means being restrained in a position in which it does not bear on the container and releasable on inhalation through the device to a position in which it does bear on the container.

The chamber adapted to receive the container is conveniently formed as a generally cylindrical chamber and is preferably formed in at least two separable parts, e.g. with a screw thread, bayonet or similar mounting, to enable the container to be changed as and when necessary.

As will be apparent, the device has suitable air inlet(s) and a mouthpiece or nosepiece respectively to entrain the material dispensed from the container and to enable it to be inhaled by a patient. Preferably, the air flow through the device is through the chamber around the container which is preferably a loose fit in the chamber.

The actuating means for the container valve mechanism is preferably mounted fixedly in the device so that it remains stationary and bears on the valve mechanism of the container at all normal times. The container moves relative thereto to dispense material from the container. The outlet from the container is desirably provided with a spray head adapted to produce a suitable spray pattern and direction and the actuating means conveniently bears on the spray head or incorporates a spray forming nozzle in flow communication with the outlet to the container. It is particularly preferred that the valve mechanism be biassed into the closed position and that it be of the metered dose form.

The first and second biassing means are both preferably helical compression springs, although other means, e.g. leaf springs or an over centre biassed leaf spring, may be employed if desired. It is preferred that the springs bear against the base of the container to urge it upward (i.e. longitudinally) within the chamber and against the valve actuating means. Preferably the two springs are mounted substantially co-axially with one another and with the longitudinal axis of the chamber.

The first biassing means preferably bears at all normal times on the container, and preferably provides from 30 to 80%, especially 50 to 75%, of the force required to depress the valve mechanism of the container. Typically, with a conventional medicament-containing container, the load required to depress the valve mechanism thereof on its own and ignoring effects from other components of the container is from 2.0 to 2.5 kg, and the percentages quoted above may reasonably be calculated based on these load figures. The second biassing means preferably also provides from 30 to 80%, especially 50 to 75%, of the force required to depress the valve mechanism of the container. The sum of the forces exerted by the first and second biassing means is preferably from 120 to 140% of the force required to depress the valve mechanism of the container.

The second biassing means is latched in a non-operative position out of contact with the container until the latch is released by the patient inhaling. The latching can be achieved by any convenient means. The latch may be released manually if desired, e.g. by means of a push-button/lever system. However, it is preferred for the latch to be released by means of a pressure sensitive device which moves in response to a lowering of the air pressure within the device as the patient begins to inhale therethrough. Such pressure sensitive devices include vanes and diaphragms. However, it is preferred to use a piston and cylinder, the piston moving within the cylinder when the patient inhales through the device, said movement being employed, e.g. by means of levers and pivots, to release the latch. Preferably, the air inlets into the inhalation device enter through the cylinder and only allow air to pass into the chamber and through the device when the piston has moved far enough in the cylinder to release the latch. Such an arrangement ensures that air cannot enter the device until the piston has moved and the medicament has thus been expelled from the container. This ensures that the patient is actually dosed with medicament each time he uses the device, and moreover enables him to continue to inhale air through the device after the medicament has been administered where a metering valve is used on the container to dispense a metered dose of medicament.

The movement of the pressure sensitive device may be translated into release of the latch in any conventional way, for example by a rod or lever arrangement connected therebetween. Desirably, the pressure sensitive device is biassed, e.g. by means of a spring, into a rest position wherein the latch restrains the second biassing means, and is arranged to move against the bias when the patient inhales. A push-button is desirably provided in such a construction whereby, after inhalation through the device the container can be moved manually against the bias of the first and second biasing means so as to latch the second biasing means against its bias. The device is then primed and ready to administer another dose of medicament.

When the second biassing means is released, it acts in concert with the first biassing means and the combined force thereof, being greater than that necessary to depress the portion of the valve mechanics, causes the container to move within the housing relative to the valve mechanism portion (which is held stationary by the actuating means) thereby releasing the dose of the material, e.g. a medicament, from the container. Since only the second biasing means is released on inhalation through the device, the operation thereof is more gentle than the prior art devices. The inhalation device of the invention is of especial use with metered valve aerosol cans so that a known dose of medicament can be dispensed from the can even though the outlet valve mechanism is held in the depressed position by the two biassing means.

From another aspect, this invention provides an inhalation device for use with a pressurised container having an outlet valve mechanism and from which a dose of a material can be discharged by depression of a portion of the valve mechanism, which device comprises a chamber for receiving said container; actuating means adapted to bear on the valve mechanism of the container; biasing means providing sufficient force to depress the valve mechanism portion and adapted to bear on the container to urge it towards the actuating means; latch means adapted to engage the biasing means and to restrain it in an inoperative position where it does not urge the container to depress the valve mechanism portion; and latch release means comprising a piston and cylinder assembly, said piston being adapted to move axially in the cylinder in response to a reduction of pressure within the inhalation device, and means for translating said movement into release of the latch means.

A preferred form of the device of the invention will now be described by way of illustration with respect to the accompanying drawing which is a cross-section through the device.

The inhalation device comprises an upper housing member 1, a lower housing member 2 and a base housing member 3. These housing members are provided with screwthreads 4 and 5 so that they can be connected together to form a hollow generally cylindrical housing enclosing a cylindrical chamber 6 which loosely receives a container 7 of medicament. Housing member 1 has an outlet mouthpiece 9 through which a patient can inhale medicament dispensed from container 7.

The container 7 has a valve mechanism and outlet 8 through which, when the valve mechanism is depressed relative to the container 7, a metered dose of the medicament is discharged.

Bearing on the outlet 8 to the valve mechanism of the container 7 is an axial actuating member 10 which is fixedly attached within upper housing member 1. A spray head 11 is formed within the actuating member 10 and in fluid flow communication with outlet 8 which directs the medicament from container 7 as a spray through mouthpiece 9.

Slidably mounted within lower housing member 2 is a sleeve member 12 having a transverse wall which bears on the base of the container 7 under the force of a helical compression spring 13 which acts between it and base member 3. Spring 13 exerts on the base of the container when the device is assembled as shown in the drawing, a force which is approximately 60% of that required to depress the valve mechanism of the container 7. Spring 13 thus urges the sleeve member 12 and the container 7 towards the fixed actuating member 10 without actuating the valve mechanism.

A cylindrical member 14 is mounted co-axially within base member 3 and within spring 13. Within the member 14 is slidably mounted a piston member 15. Preferably, the crown of the piston is formed as a conical surface with its apex directed axially upward. The apex 16 of the crown is attached to a rod 17 which terminates at pivot point 18. To this point 18 are pivotally attached radial pivot arms 19 and 20 which respectively terminate at pivot points 21 and 22, where they are connected pivotally to longitudinally directed latch arms 23 and 24 respectively. Latch arms 23 and 24 are themselves pivoted on fixed pivots 25 and 26 provided on the inner wall of cylinder member 14.

A cylindrical thrust member 29 is mounted co-axially within the lower housing member 7 and is adapted to bear against the underside of the transverse wall in sleeve member 12 under the influence of a coil spring 30. The lower end of spring 30 is restrained by a stepped member 31 fixedly mounted within cylindrical member 14. Latch arms 23 and 24 latch over radial projections 27 and 28 or an annular flange provided on member 29 to hold member 29 restrained from bearing against the transverse wall of sleeve member 12. Spring 30 exerts a force which is 60% of that required to actuate the valve mechanism of container 7. Thus, in combination, springs 13 and 30 exert sufficient force to actuate the valve mechanism but the latch mechanism effectively prevents spring 30 acting on the container 7. Between the member 31 and the pivot point 18 is provided a further helical spring 32 which biasses the piston member 15 towards the base housing member 3 and hence splays the arms 19 and 20 radially to cause the latch arms 23 and 24 to assume their operative position and engage projections 27 and 28.

In use, the mouthpiece 9 of the inhalation device is placed in the mouth of the patient who inhales therethrough. The air pressure within chamber 6 is reduced, and this causes piston member 15 to move axially upward within cylinder member 14 against the bias of spring 32. Air enters the space between the piston member and the base member 3 through air inlets 33 and 34 provided in said base member. The movement of the piston member 15 and associated rod 17 causes pivot point 18 to rise and, via pivot arms 19 and 20, pivot points 21 and 22 to move radially inward towards one another. This in turn causes latch arms 23 and 24 to pivot about points 25 and 26 and to release thrust member 29. Thrust member 29 then bears on sleeve member 12 which is free to slide within lower housing member 2 and bear on the base of container 7. The combined forces of springs 13 and 30 bear on the container 7 which accordingly moves axially relative to its outlet 8 which actuates its valve mechanism to discharge a metered dose of medicament through spray head 11.

As piston member 15 moves within cylinder member 14, it reaches a point where air inlets 35 and 36 provided through the wall of member 14 are uncovered. Air from inlets 33 and 34 may pass therethrough into chamber 6, past the container 7, and into mouthpiece 9 to entrain the dose of medicament discharged from the container. The entrained dose is inhaled by the patient.

When inhalation ceases, piston member 15 returns under the influence of spring 32 to the position shown in the drawing. It is then necessary to depress thrust member 29 until the latch arms 23 and 24 engage the projections 27 and 28. This can be done in a number of ways, but a convenient method is to provide the end wall of housing member 1 with a spring loaded button 37 carrying dependant arms 39 and 40. When button 37 is depressed, arms 39 and 40 bear against the top of container 7 and force it, the sleeve member 12 and the thrust member 29 towards the base housing member 3 against the actions of springs 13 and 30. The projections 27 and 28 on thrust member 29 latch under latch arms 23 and 24 and the push button 37 is released to return under the influence of spring 38 to the position shown. The device is now cocked and ready for use again. Alternatively, the device can remain in the uncocked position until the next dosage of medicament is required.

We claim:

1. An inhalation device for use with a pressurised container having an outlet valve mechanism and from which material may be discharged by depression of a portion of the valve mechanism thereof, which device comprises a chamber for receiving said pressurised container; a mouthpiece communicating with said chamber and an air flow passage means through said chamber and mouthpiece; actuating means adapted to bear on the valve mechanism of the container without actuating the valve mechanism; and first and second biasing means both adapted to bias the container towards the actuating means, said first and second biasing means each being of insufficient force alone to depress the portion of the valve mechanism of the container against the actuating means but together being of sufficient force to do so, said first biasing means being positioned to provide a continuous bias on the container toward said actuating means; and means for restraining said second biasing means in a position in which it does not bear on the container and releasing said second biasing means on inhalation through the device to a position in which it does bear on the container.

2. A device as claimed in claim 1 wherein the biasing means comprise coil springs.

3. A device as claimed in claims 1 wherein the chamber contains a pressurised container and air is capable of flowing through the chamber and around the container.

4. A device as claimed in claim 3 wherein the container is provided with a metered dose valve mechanism.

5. A device as claimed in claim 1 wherein the chamber is provided by a generally cylindrical housing in which the container is to be mounted with its longitudinal axis substantially co-axial with the longitudinal axis of the housing and the biassing means are mounted substantially co-axially within the housing and in tandem with container so as to bias the container longitudinally in the chamber towards the actuating means.

6. A device as claimed in claim 1 wherein each of the first and second biasing means is individually capable of exerting from 30 to 80% of the force required to actuate the valve mechanism of the container and together are capable of exerting from 120 to 140% of the force required to actuate the valve mechanism.

7. A device as claimed in claim 1 wherein the second biassing means is released from its inoperative position by a latching mechanism which is actuated by a pressure sensitive mechanism which is adapted to move in response to a reduction in pressure within the device whereby the second biassing means can move to urge a container mounted in chamber towards the actuation means.

8. A device as claimed in claim 7 wherein the pressure sensitive mechanism comprises a piston moveably mounted in a cylinder, the relative movement of the piston and cylinder being adapted to release the means restraining the second biasing means.

9. A device as claimed in claim 7 wherein there are provided air inlets whereby air may flow through the device via the chamber to an outlet and the passage of air through the device is obstructed by the pressure sensitive mechanism until the mechanism has moved to release the second biasing means.

10. An inhalation device for use with a pressurised container having an outlet valve mechanism and from which a dose of a material can be discharged by depression of a portion of the valve mechanism, characterised in that the device comprises a chamber (6) for receiving a pressurized container (7); a mouthpiece communicating with said chamber and an air flow passage means through said chamber and mouthpiece; actuating means (10) adapted to bear on the valve mechanism (8) of the container (7) without actuating the valve mechanism; first and second biasing means (13 and 30) adapted to bear on the container (7) to urge it towards the actuating means (10); said first and second biasing means each being of insufficient force alone to depress the portion of the valve mechanism of the container against the actuating means but together being of sufficient force to do so, said first biasing means being positioned to provide a continuous bias on the container toward said actuating means; latch means (23 and 24) adapted to engage the second biasing means (30) but not the first biasing means and to restrain the second biasing means in an inoperative position where it does not urge the container (7) toward the actuating means to depress the valve mechanism (8); and latch release means comprising a piston (15) slidably positioned in cylinder (14) assembly mounted within said chamber (6), said piston (15) being adapted to move axially in the cylinder (14) in response to a reduction of pressure caused by inhalation through the device, and means for translating said movement into release of the latch means (23 and 24) to permit the second biasing means along with the first biasing means to urge the container toward the actuating means and thereby actuate said valve mechanism.

* * * * *